United States Patent [19]

Peterson

[11] 4,257,960

[45] Mar. 24, 1981

[54] PREPARATION OF FURAN COMPOUNDS

[75] Inventor: Marvin L. Peterson, Woodstown, N.J.

[73] Assignee: E. I. Du Pont de Nemours and Company, Wilmington, Del.

[21] Appl. No.: 145,583

[22] Filed: May 1, 1980

[51] Int. Cl.$^3$ ............................................. C07D 307/36
[52] U.S. Cl. ................................................. 260/346.11
[58] Field of Search .................................... 260/346.11

[56] References Cited

U.S. PATENT DOCUMENTS 4,172,838   10/1979   Garnett et al. .................. 260/346.11

*Primary Examiner*—Richard Raymond

[57] ABSTRACT

Furan compounds are prepared by converting butenediols, using a redox system which is an aqueous solution containing copper having an average oxidation state of between 1 and 2, a solubilizing agent for $Cu^{+1}$ ions, and 0.05–2.00 moles per liter of hydrogen ions.

13 Claims, No Drawings

PREPARATION OF FURAN COMPOUNDS

BACKGROUND OF THE INVENTION

1. Field of the Invention

This invention relates to a process for preparing furan compounds from unsaturated diols, ethers or esters. It is more particularly directed to such a process in which a copper redox system is used as a reactant.

SUMMARY OF THE INVENTION

According to the invention, a butenediol, -ether (aliphatic or cyclic) or -ester, or a vinyl dioxane, is converted to a furan compound, using a redox system which comprises (1) water as the solvent,
(2) copper having an average oxidation state between 1 and 2,
(3) a solubilizing agent for cuprous ions, soluble in water and capable of forming a water-soluble complex with cuprous ions, and (4) 0.05–2.00 moles per liter of hydrogen ions.

The furan compound product is removed from the reaction mass by sweeping it with an inert gas such as nitrogen, and the furan compound is then separated from the gas stream by conventional techniques.

The process of the invention proceeds according to the following schematic equations:

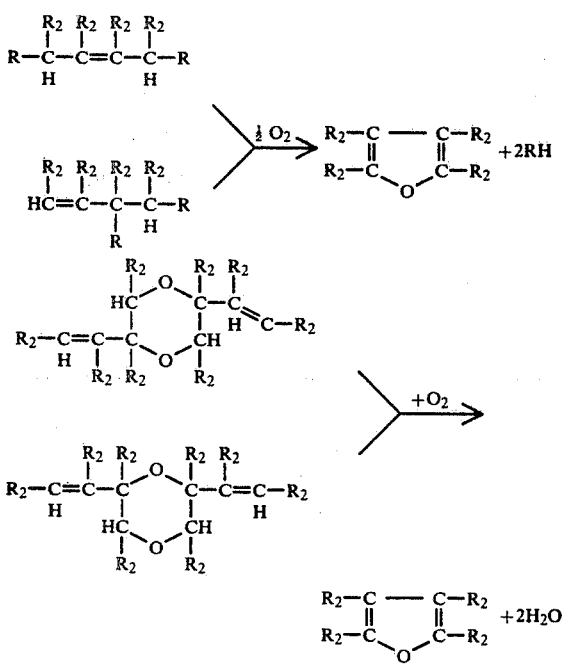

DETAILED DESCRIPTION OF THE INVENTION

The starting materials used, i.e., those compounds which are converted to furan compounds by the process of the invention, can be any of those represented by the structures

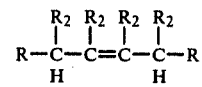

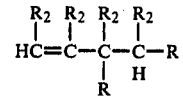

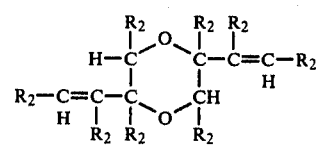

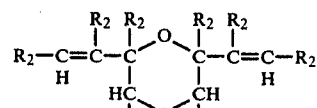

or

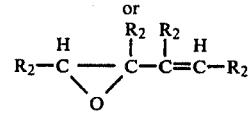

where
R is —OH, —OR$_1$ or

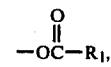

R$_1$ is an alkyl radical of 1–4 carbon atoms, and
R$_2$ is hydrogen or an alkyl radical of 1–4 carbon atoms.

Both the cis and trans isomers of these compounds can be used.

Illustrative of these starting materials are
2-butene-1,4-diol
1-butene-3,4-diol
1,4-diacetoxy-2-butene
3,4-dimethoxy-1-butene
1,4-dimethoxy-2-butene
2,5-divinyl-1,4-dioxane
2,6-divinyl-1,4-dioxane
2-methyl-2-butene-1,4-diol
2-pentene-1,4-diol.

The starting materials preferred for use are 2-butene-1,4-diol (cis and trans) and 1-butene-3,4-diol.

The redox system used comprises water as the solvent, copper ions, and a solubilizing agent to keep the requisite number of Cu$^{+1}$ ions in solution.

It is preferred that water be used as the sole solvent or carrier for the system, but liquids in which water is diluted with up to 50%, by volume, of a hydrophilic solvent such as acetic acid, sulfolane, acetonitrile, dioxane or the like can also be used.

Both Cu$^{+1}$ and Cu$^{+2}$ ions must be present in the system, i.e., the copper must have an average oxidation state between 1 and 2, preferably between 1.3 and 1.90. As the process proceeds, the Cu$^{+2}$ ions are reduced to Cu$^{+1}$ ions, and the reaction slows or stops entirely until some of the Cu$^{+1}$ ions are oxidized back to Cu$^{+2}$ ions, as will be described later.

Copper ions are present in the system at a total concentration of about 0.1–10 moles per liter, preferably 0.5-3.5 moles per liter, and in $Cu^{+2}/Cu^{+1}$ mole ratios of 100/1 to ½, preferably 10/1 to ½.

The copper ions can be supplied by any water-soluble copper compound. Salts of the organic acids can be used; halides are preferred, and chlorides are especially preferred. Salts of organic acids such as formic, acetic, propionic, trifluoroacetic, methanesulfonic, benzenesulfonic and p-toluenesulfonic can also be used. Mixtures of acids can also be used.

The solubilizing agent in the system can be any water-soluble inorganic or organic compound which forms a complex with $Cu^{+1}$ ions soluble enough in water to form a 0.2-3 molar solution. Illustrative of such agents are alkali metal halides
alkaline earth metal halides
ammonium halides
iron halides
halogen acids
organic nitriles such as acetonitrile and succininitrile
carboxylic acids such as acetic acid thiocyanates such as sodium thiocyanate aliphatic amines such as tetramethylenediamine.

Solubilizing agents preferred for use are the alkali metal halides and the ammonium halides. Sodium chloride, potassium chloride, calcium chloride and ammonium chloride are especially preferred. Mixtures of solubilizing agents can also be used.

The solubilizing agent is present in the system at a concentration of about 0.01-5 moles per liter, preferably 0.3-5 moles per liter.

The redox system must be acidic. It is not possible to accurately express acidity of the system in terms of conventional pH values because the copper ions present interfere with pH measurements by the potentiometric method ordinarily used. Acidity of the system is therefore expressed in terms of hydrogen ion concentration, as measured by conventional titration techniques with standard base solutions, using such indicators as methyl red or methyl orange to determine end-point, as is well-known in the art.

The redox system should have a hydrogen ion concentration of 0.05-2 moles per liter, preferably 0.1-1 mole per liter. The hydrogen ions can be supplied by any acid which does not interfere with the reaction. Hydrochloric acid is preferred.

The process of the invention can be run intermittently or continuously. In the intermittent operation, a reaction vessel, made of material capable of withstanding the possible corrosive effects of the copper salts used, is charged with the redox system, which also functions as the reaction medium. The redox system is prepared by simply dissolving suitable amounts of copper salts, solubilizing agent and acid in an appropriate amount of water.

The solution is then brought to and held at a temperature of 80°-150° C., preferably 90°-105° C., with stirring, while the starting material is slowly fed in until the reaction slows or stops due to the lack of $Cu^{+2}$ ions.

Simultaneously with the starting material feed, the reaction mass is swept with an inert gas, preferably by bubbling it through. This agitates the mass, and the gas stream carries the furan compound out of the reactor as it is formed.

The gas used can be any that is inert to the reaction. Nitrogen, helium, water vapor and carbon dioxide are illustrative; nitrogen is preferred. The gas is fed into the reactor at a rate that will maintain about atmospheric pressure.

The furan compound product can be separated from the gas stream by any convenient technique, and is most easily done by condensation with conventional equipment. The gas can then be recycled if desired.

When the reaction has slowed or stopped, it is necessary to replenish the redox system with $Cu^{+2}$ ions. This is done by passing oxygen through the system. The oxygen can be introduced as molecular oxygen, or as a mixture of oxygen with other gases. For example, air can be used, or oxygen can be mixed with the inert gas used. The replenishment can be done in situ or can be carried out in a separate reactor. Oxygenation is continued until oxidation of the $Cu^{+1}$ ions to $Cu^{+2}$ ions has brought the $Cu^{+2}/Cu^{+1}$ ratio to the original level, as determined potentiometrically. The process can then be begun anew.

In continuous operation, the process is also begun by charging the reactor with the redox system. This is then brought to and held at 80°-150° C., preferably 90°-105° C., and stirred while starting material is fed in the rate of 0.0025-0.015 mole per liter per minute.

At the same time, a mixture of oxygen and inert gas, preferably nitrogen, in an oxygen/nitrogen weight ratio of 10-50/90-50, is fed into the reaction mass, again preferably by bubbling it through. This simultaneously removes furan product from the mass as it forms and replenishes the redox system. The gas mixture is fed into the mass at a rate predetermined to maintain the original $Cu^{+2}/Cu^{+1}$ ratio, as measured potentiometrically.

Furan compound product is continuously removed from the gas stream, preferably by condensation. The gas can be recycled if desired.

EXAMPLES

In these examples, all parts are by volume.

EXAMPLE 1—BEST MODE

Into a reactor of 500 parts capacity were charged 250 parts of an aqueous redox system containing, in addition to water,

| | |
|---|---|
| $CuCl_2$ | 1.2 moles/liter |
| CuCl | 1.6 moles/liter |
| $NH_4Cl$ | 2.4 moles/liter |
| HCl | 0.72 mole/liter |

This solution was stirred at about 2000 rpm, then heated to and held at about 100° C.

Separate streams of nitrogen at 200 parts per minute and oxygen at 35 parts per minute were fed into the solution while cis-2-butene-1,4-diol was fed in at the rate of 0.05 part (0.00059 mole) per minute, to produce furan at the rate of 0.00056 mole per minute.

The gas stream was continuously withdrawn from the reactor and product furan was continuously condensed from it by means of a trap cooled with dry ice.

EXAMPLE 2

The procedure used was that described in Example 1. The redox system contained, in addition to water,

| | |
|---|---|
| $CuCl_2$ | 2.0 moles/liter |
| CuCl | 1.2 moles/liter |
| $CaCl_2$ | 1.2 moles/liter |

| | |
|---|---|
| -continued | |
| HCl | 0.62 mole/liter |

Trans-2-butene-1,4-diol was fed into the solution at the rate of 0.1 part per minute. Furan was produced at the rate of 0.0008 mole per minute.

EXAMPLE 3

The procedure used was that described in Example 2. 1-Butene-3,4-diol was introduced into the solution at the rate of 0.1 part (0.0012 mole) per minute and furan was produced at the rate of 0.00087 mole per minute.

EXAMPLE 4

The procedure used was that described in Example 2. 1,4-Diacetoxy-2-butene was introduced into the solution at the rate of 0.2 part (0.00116 mole) per minute. Furan was produced at the rate of 0.00087 mole per minute.

INDUSTRIAL APPLICABILITY

The process of the invention can be used to produce furan, a commodity in the chemical industry, widely used as an intermediate in the production of tetrahydrofuran.

I claim:

1. A process for the preparation of a furan compound, the process comprising (A) bringing together, under conditions suitable for furan compound formation, (1) a compound represented by the structure

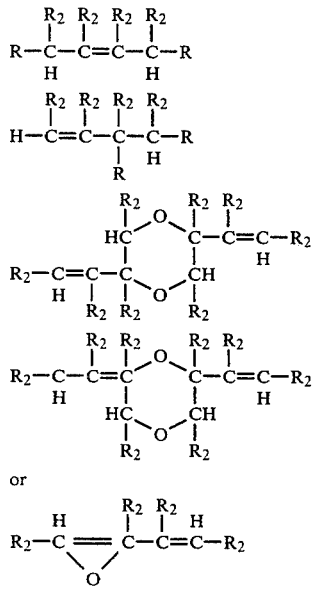

where

R is —OH, —OR$_1$ or

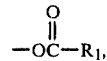

$R_1$ is an alkyl radical of 1-4 carbon atoms, and
$R_2$ is hydrogen or an alkyl radical of 1-4 carbon atoms, (2) a solution comprising
  (a) water as the solvent,
  (b) copper having an average oxidation state between 1 and 2,
  (c) a solubilizing agent for cuprous ions, soluble in water and capable of forming a water-soluble complex with cuprous ions, and
  (d) 0.05-2.00 moles per liter of hydrogen ions, and (B) separating furan compound from the resulting reaction mass.

2. The process of claim 1 in which the compound in (A) (1) (a) is 2-butene-1,4-diol.

3. The process of claim 1 in which the compound in (A) (1) (b) is 1-butene-3,4-diol.

4. The process of claim 1 in which the copper ions are derived from CuCl and CuCl$_2$.

5. The process of claim 1 in which the solubilizing agent is an alkali metal halide, an alkaline earth metal halide or an ammonium halide.

6. The process of claim 1 in which the solubilizing agent is sodium chloride, potassium chloride, calcium chloride or ammonium chloride.

7. The process of claim 1 in which the separation in (B) is accomplished by sweeping the reaction mass with an inert gas and then condensing furan from the gas stream.

8. The process of claim 7 conducted in a continuous fashion.

9. The process of claim 1 in which the concentration of copper ions in solution (2) is 0.1-10 moles per liter.

10. The process of claim 1 in which the $Cu^{+2}/Cu^{+1}$ ratio is $100/1\frac{1}{2}$.

11. The process of claim 1 in which step (A) is carried out at a temperature of 80°–150° C.

12. The process of claim 1 having the added step of converting $Cu^{+1}$ ions in the reaction mass to $Cu^{+2}$ ions by bringing the mass into intimate contact with an oxygen-containing gas.

13. A process for the preparation of furan, the process comprising (A) continuously bringing together 2-butene-1,4-diol or 1-butene-3,4-diol and an aqueous solution comprising
  (1) 0.1–10 moles per liter of $Cu^{+1}$ and $Cu^{+2}$ ions, the $Cu^{+2}/Cu^{+1}$ mole ratio being $100/1\frac{1}{2}$,
  (2) 0.01–5 moles per liter of ammonium chloride, and
  (3) 0.05–2.00 moles per liter of hydrogen ions, at a temperature of 80°–150° C., (B) continuously removing furan from the reaction mass and holding the $Cu^{+2}/Cu^{+1}$ ratio in the mass at about the original level by sweeping it with an oxygen-containing gas, and then (C) separating furan from the gas stream by condensation.

* * * * *